United States Patent
Krotseng

[11] Patent Number: 5,993,590
[45] Date of Patent: Nov. 30, 1999

[54] METHOD FOR COATING OBJECTS WITH SILICONE

[75] Inventor: Kathryn G. Krotseng, Richmond, Va.

[73] Assignee: Manni-kit, Inc., Richmond, Va.

[21] Appl. No.: 08/886,314

[22] Filed: Jul. 1, 1997

[51] Int. Cl.$^6$ ............................ B44C 1/165; B29B 1/165; B32B 31/00; A61F 2/52

[52] U.S. Cl. ........................ 156/230; 156/232; 156/242; 156/245; 156/246; 156/247; 156/244.27; 264/321; 623/7

[58] Field of Search ..................................... 156/242, 245, 156/246, 247, 289, 232, 78, 230, 244.27; 83/19; 264/46.4, 159, 259, 321, 338, 48, 451; 427/2.24; 623/7, 10, 155

[56] References Cited

U.S. PATENT DOCUMENTS

| | | |
|---|---|---|
| 2,565,524 | 8/1951 | Rust et al. . |
| 2,606,398 | 8/1952 | Miller . |
| 2,686,747 | 8/1954 | Wurtz et al. . |
| 2,765,248 | 10/1956 | Beech et al. ............................. 156/232 |
| 2,772,194 | 11/1956 | Fisher et al. ............................ 156/232 |
| 3,432,581 | 3/1969 | Rosen . |
| 3,456,046 | 7/1969 | Rosen . |
| 3,541,192 | 11/1970 | Shapero et al. . |
| 3,665,792 | 5/1972 | Bush et al. . |
| 3,844,862 | 10/1974 | Sauer et al. ............................... 156/78 |
| 3,865,284 | 2/1975 | Kazama et al. . |
| 3,872,194 | 3/1975 | Lowry et al. . |
| 4,036,673 | 7/1977 | Murphy et al. . |
| 4,265,851 | 5/1981 | Roth . |
| 4,418,157 | 11/1983 | Modic . |
| 4,451,416 | 5/1984 | Burtscher ............................... 264/46.6 |
| 4,492,775 | 1/1985 | Koshii et al. . |
| 4,495,227 | 1/1985 | Tanaka . |
| 4,559,369 | 12/1985 | Bauman et al. . |
| 4,572,917 | 2/1986 | Graiver . |
| 4,590,222 | 5/1986 | Bauman . |
| 4,656,906 | 4/1987 | Mozieka et al. . |
| 4,704,408 | 11/1987 | Krug et al. . |
| 4,728,567 | 3/1988 | Razzano et al. . |
| 4,760,098 | 7/1988 | Miutel . |
| 4,767,794 | 8/1988 | Modic et al. . |
| 4,793,530 | 12/1988 | Krotseng . |
| 4,808,634 | 2/1989 | Uriarte et al. . |
| 4,810,728 | 3/1989 | Gross et al. . |
| 4,840,974 | 6/1989 | Gross et al. . |
| 4,877,814 | 10/1989 | Ito . |
| 4,879,317 | 11/1989 | Smith et al. . |
| 4,888,217 | 12/1989 | Jones . |
| 4,889,744 | 12/1989 | Quaid . |
| 4,983,641 | 1/1991 | Gross et al. . |
| 4,983,642 | 1/1991 | Nakano et al. . |
| 4,987,155 | 1/1991 | Inoue et al. . |
| 5,011,865 | 4/1991 | Johnson . |
| 5,017,624 | 5/1991 | Johnson . |

(List continued on next page.)

FOREIGN PATENT DOCUMENTS

| | | |
|---|---|---|
| 2172766 | 3/1997 | Canada . |
| 2243324 | 10/1991 | United Kingdom ............ B29C 39/10 |

OTHER PUBLICATIONS

Kander et al. "Optimization of Low Density Silicone Foam Process–Structure–Property Relationships", Viginia Polytechnic Institute & State University, pp. 1–29, Jun. 13, 1994.

RTF 762 General Electric Silicone Product Data (Nov. 1985).

*Primary Examiner*—Richard Crispino
*Assistant Examiner*—J. A. Lorengo
*Attorney, Agent, or Firm*—J. Michael Martinez de Andino; McGuire, Woods, Battle & Boothe, LLP

[57] ABSTRACT

A method for coating objects with silicone that includes the steps of preparing the silicone material; applying the silicone material onto a surface that is resistant to adhesion to silicone, such as an acetate film layer or the inside surface of an open air mold; allowing the silicone material to sufficiently cure to allow for bonding to an object; pressing the object against the silicone material; allowing the silicone material to bond to the outer surface of the object; and then removing the object from the surface resistant to adhesion to the silicone material.

23 Claims, 8 Drawing Sheets

U.S. PATENT DOCUMENTS

| | | |
|---|---|---|
| 5,019,295 | 5/1991 | Yoshida et al. . |
| 5,041,466 | 8/1991 | Takahashi et al. . |
| 5,066,259 | 11/1991 | Acker . |
| 5,098,782 | 3/1992 | Hovis et al. . |
| 5,106,548 | 4/1992 | Matsuura et al. . |
| 5,153,231 | 10/1992 | Bouquet et al. . |
| 5,194,311 | 3/1993 | Baymak et al. . |
| 5,246,974 | 9/1993 | Jones et al. . |
| 5,271,736 | 12/1993 | Picha . |
| 5,296,069 | 3/1994 | Robert ................................. 156/242 |
| 5,352,307 | 10/1994 | Wild ..................................... 156/66 |
| 5,356,940 | 10/1994 | Giesen . |
| 5,391,583 | 2/1995 | Blount . |
| 5,409,648 | 4/1995 | Reidel ................................. 264/45.1 |
| 5,508,321 | 4/1996 | Brebner . |
| 5,549,858 | 8/1996 | Krotseng . |

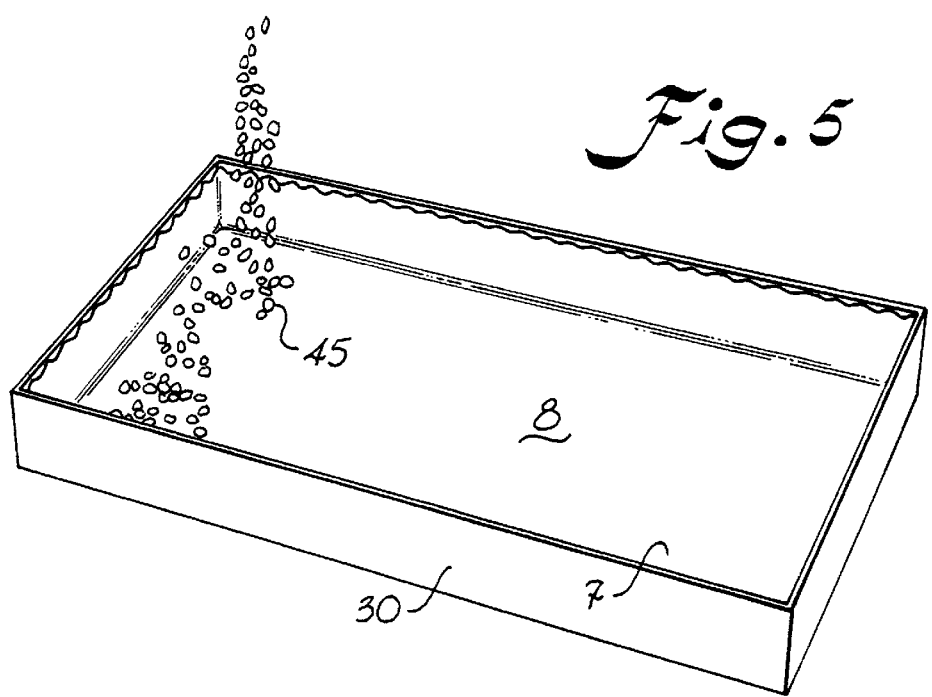
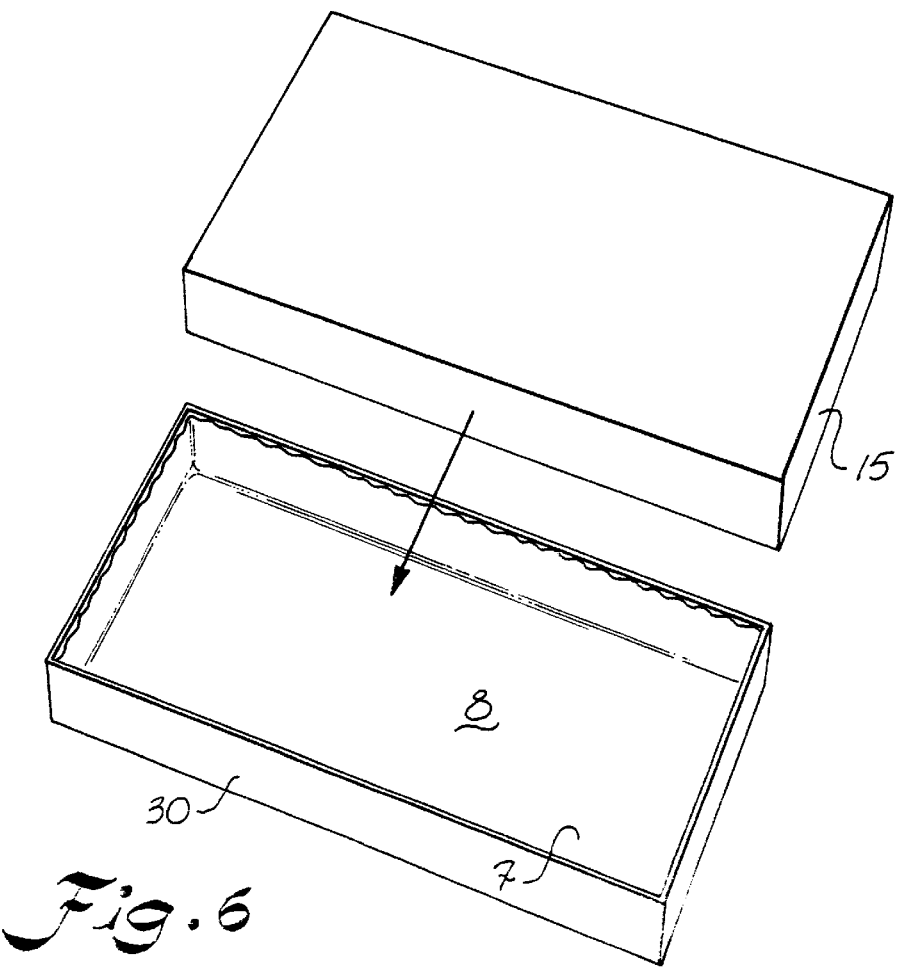

METHOD FOR COATING OBJECTS WITH SILICONE

FIELD OF THE INVENTION

This invention relates to a method for applying a layer of silicone to an object, but more specifically, to a method for applying a layer of silicone foam or silicone rubber to an object having a porous surface and to a method for applying a layer of silicone foam or silicone rubber to an object having a porous surface giving the underlining porous surface core a designed surface skin.

BACKGROUND OF THE INVENTION

Conventional methods employed to apply or mold silicone onto preformed objects encounter several problems. One such problem is the requirement to have an external heat source to help cure a layer of silicone foam to fabric as set forth in U.S. Pat. No. 4,495,227. Other problems evident when using conventional methods include the need to use of a layer of cement to attach the sealing silicone material to an object to be covered as set forth in U.S. Pat. No. 2,666,747.

There are also conventional methods for producing a silicone foam backed plastic film or metal foil to product a flame-retardant material as set forth in U.S. Pat. No. 4,728,567. However, the 567 Patent flame retardant material is not described or disclosed to be used to transfer the silicone foam material to a separate object for providing a uniform layer of silicone foam to the separate object. Further, there are conventionally known compositions for producing a bondable and sealable silicone composition that can be used to seal or cover objects, such as the composition set forth in U.S. Pat. No. 5,246,974. The 974 Patent disclosed silicone foam composition that is heat resistant and which can be used for covering walls and overheads, or for making bodies from the claimed composition. Similarly, the silicone foam described in U.S. Pat. No. 5,356,940 is claimed to be directed to a foam that can be used to make heat shields by lining aluminum foil with the produced foam. The 947 Patent and 940 Patent do not explain or describe how to make a smooth layer of silicone foam or rubber surface with a specific design that is applied to a material resilient to silicone adhesion for later pressing the foam material against other objects for bonding the layer to the other object.

Additionally, conventional methods employed to mold silicone foam into large shapes encounter several problems. By using the disclosed method for coating objects with silicone a silicone skin layering process is described that includes applying pre-determined amounts of a silicone foam or rubber material into a detailing mold to produce an outer layer, and sealing and adhering the outer layer to an object to create a silicone skin layered object. The silicone skin layered object can be formed to have various shapes and sizes having a low density, uniform cell structure with a smooth outer skin.

It has been discovered in accordance with the invention described below that a low density, lightweight, buoyant, fire-resistant, non-toxic, non-acidic and non-corrosive alternative to plastics or polyurethane is presently available through the curing of silicone foam or silicone rubber and applying the curing silicone foam or silicone rubber to an object having a porous surface for applying the curing material to a separate preformed object for applying a uniform layer of silicone foam with designed characteristics for texture or other physical characteristics.

OBJECTS OF THE PRESENT INVENTION

Accordingly, it is the primary object of the present invention to provide a method for applying a uniform layer of silicone foam or silicone rubber with designed characteristics for texture or other physical characteristics to objects.

It is another object of the invention to provide a method for applying a uniform layer of silicone foam or silicone rubber with designed characteristics for texture or other physical characteristics to objects wherein the method includes the step of applying a layer of silicone material to a material resistant to silicone foam adhesion (referred to as the "Silicone Resistant Material") which is then used for applying the layer of silicone material to a preformed object.

It is another object of the invention to provide a method for applying a uniform layer of silicone foam or silicone rubber with designed characteristics for texture or other physical characteristics to objects wherein the method includes the steps of applying a layer of silicone material to a Silicone Resistant Material, using the coated resistant material for applying the layer of silicone material to a preformed object, and then removing the Silicone Resistant Material from the layer of silicone that has bonded to the preformed object.

It is a further object of the invention to provide a method for applying a uniform layer of silicone foam or silicone rubber with designed characteristics for texture or other physical characteristics to objects, wherein the method includes the steps of applying a layer of silicone material into a detailing mold to produce an outer layer; the sealing and adhering of the outer layer to an object to create a silicone skin layered object; and connecting and fastening several above-identified silicone skin layered objects to produce a designated shape.

Other objects and advantages of this invention will become apparent from the following description taken in connection with the accompanying drawings wherein are set forth, by way of illustration and example, certain embodiments of this invention.

DESCRIPTION OF THE DRAWINGS

FIG. 5 is a top plan view of the open mold of FIGS. 4A and 4B having chopped or cut particles of additional cushioning material being spread on top of the layer of silicone.

FIG. 6 is an exploded isometric view showing a preformed object being placed within the open mold of FIG. 5 for covering the bottom and sides of the preformed object with the layer of silicone.

DETAILED DESCRIPTION OF THE INVENTION

Before the present invention is described, it is to be understood that this invention is not limited to a method of applying silicone foam or silicone rubber, as such may, of course, vary. It is also to be understood that the terminology used herein is for the purpose of describing particular embodiments only, and is not intended to be limiting as the scope of the present invention will be limited only by the appended claims.

Figure 1A:
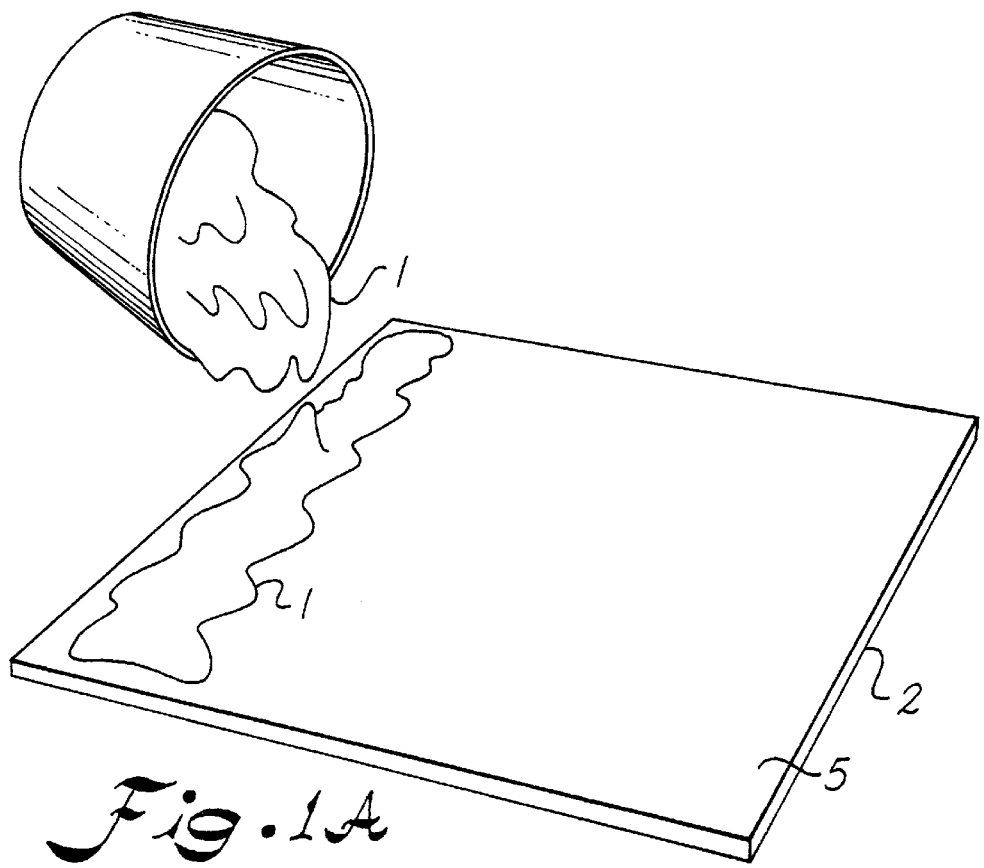
FIGS. 1A and 1B are perspective views of silicone foam or silicone rubber being applied to a Silicone Resistant Material and then being spread to form a layer of silicone through the use of a blade.
Figure 2:
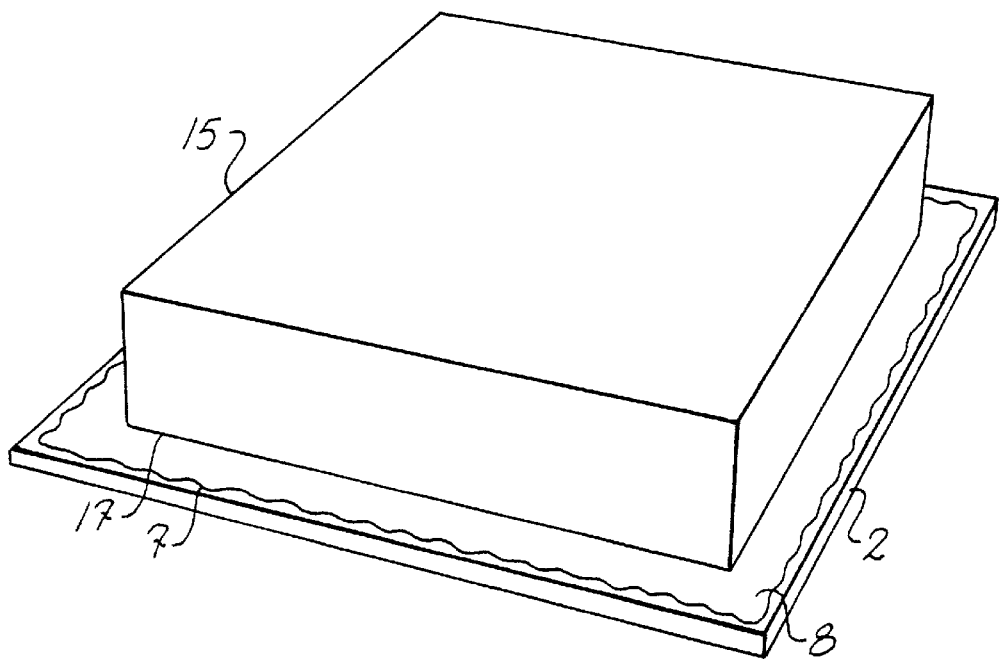
FIG. 2 is a perspective view of a preformed object being pressed against the exposed surface of the layer of silicone.

Unless defined otherwise, all terms used herein have the same meaning as commonly understood by one of ordinary skill in the art to which this invention belongs. Referring now to the drawings, in FIG. 1A there is illustrated the applying silicone foam or silicone rubber material 1 onto the top surface 5 of a material 2 resistant to silicone adhesion ("Silicone Resistant Material 2"). The silicone material 1 is formulated to reflect the needs required by the object or core material 15 to be foamed, which is shown in FIG. 2. The silicone material 1 can be, but is not limited to, being formulated in accordance with the instructions set forth in the General Electric Silicone Product Data Sheets RTF 762, RTF 7000, RTV 660, RTV 662, RTV 664, RTV 666 or RTV 700 for Silicone Rubber Foam. When preparing the silicone material 1, factors such as the friction resistance, chemical resistance and the ultraviolet resistance of the core material 15 need to be considered. Additionally, the silicone material 1 can have materials imbedded in it, such as reflective or absorbent materials, and/or materials that can conduct and/or sense pressure, electricity and/or light.

Figure 1B:
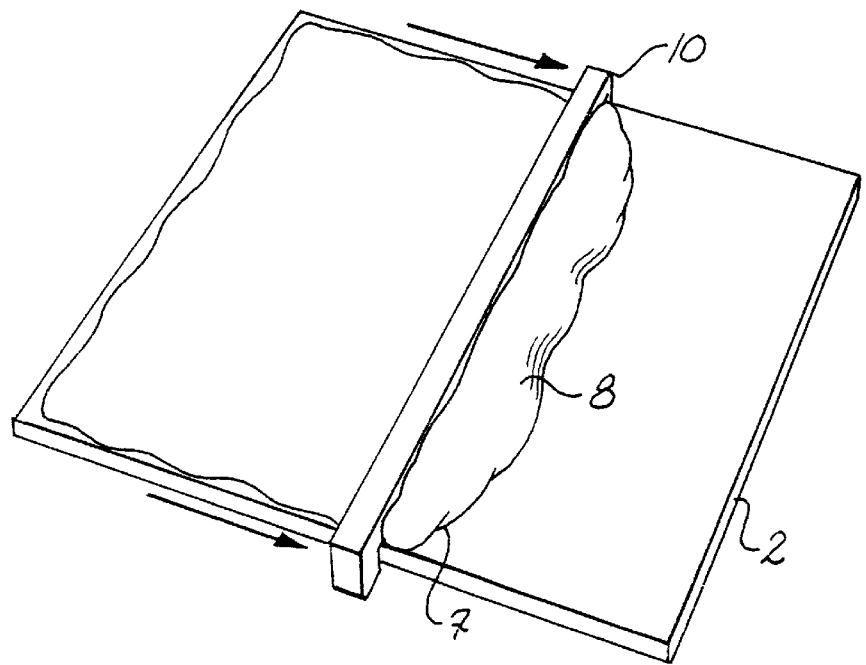

Examples of a Silicone Resistant Material 2 include, but are not limited to, a sheet or film made from acetate, plastic or any material that allows cured silicone foam or silicone rubber to easily peel off from the resistant film or material. Additionally, the Silicone Resistant Material 2 can have ridges or indentations on its surfaces, be flexible or stiff, and/or have a design formed on its surface such that when the silicone material 1 is placed on the Silicone Resistant Material 2, the resulting silicone layer 7 can acquire the inverse features of the top surface 5 of the silicone resistant material 2. Further, the Silicone Resistant Material 2, if flexible, can be molded around a number of shapes, such as a square, cylinder or a curved object. As shown in FIG. 1B, the silicone material 1 is spread, sprayed or otherwise applied to form a designed thickness on the Silicone Resistant Material 2 through the use of a blade 10. The thickness of the silicone material 1 being applied to the Silicone Resistant Material 2 is dependent on the specific requirements of the desired layer of the silicone material 1 that is to be applied to the material 15. For example, the thickness of the silicone material 1 can be approximately $\frac{1}{32}$ of an inch to one or more inches. The desired thickness of the silicone material 1 can be set by adjusting the height of the blade 10 above the top surface 5 of the Silicone Resistant Material 2. The blade edge 10 spans the width of the Silicone Resistant Material 2 and as the blade edge 10 is guided across the Silicone Resistant Material 2, it spreads the silicone material 1 along the top surface 5 of the Silicone Resistant Material 2 in a designed depth and evenness to produce a silicone layer 7. The silicone layer 7 is allowed to cure for approximately thirty seconds to seven minutes. The time allowed for curing the silicone layer 7 is dependent upon the characteristics of the material 15. The silicone layer 7 should be allowed to cure such that when the material 15 is pressed against the silicone layer 7 the material 15 does not pass through the silicone layer 7 and make contact with the Silicone Resistant Material 2.

Referring now to FIG. 2, the material 15 is placed upon the top surface 8 of the silicone layer 7. The material 15 can consist of any porous material not resistant to adhesion or bonding with silicone. Examples of a material 15 can include, but are not limited to, silicone, polyurethane, neoprene, wood, wood related products, and fabrics. When placing the material 15 on the silicone layer 7, it is gently pressed against the silicone layer 7 and held in place until the silicone layer 7 has adhered or bonded to the contacting surface 17 of the material 15. The material 15 should be pressed against the silicone layer 7 for approximately twenty minutes to twenty-four hours, depending on several factors, such as the thickness of the silicone layer 7 and the size of the material 15.

Figure 3:
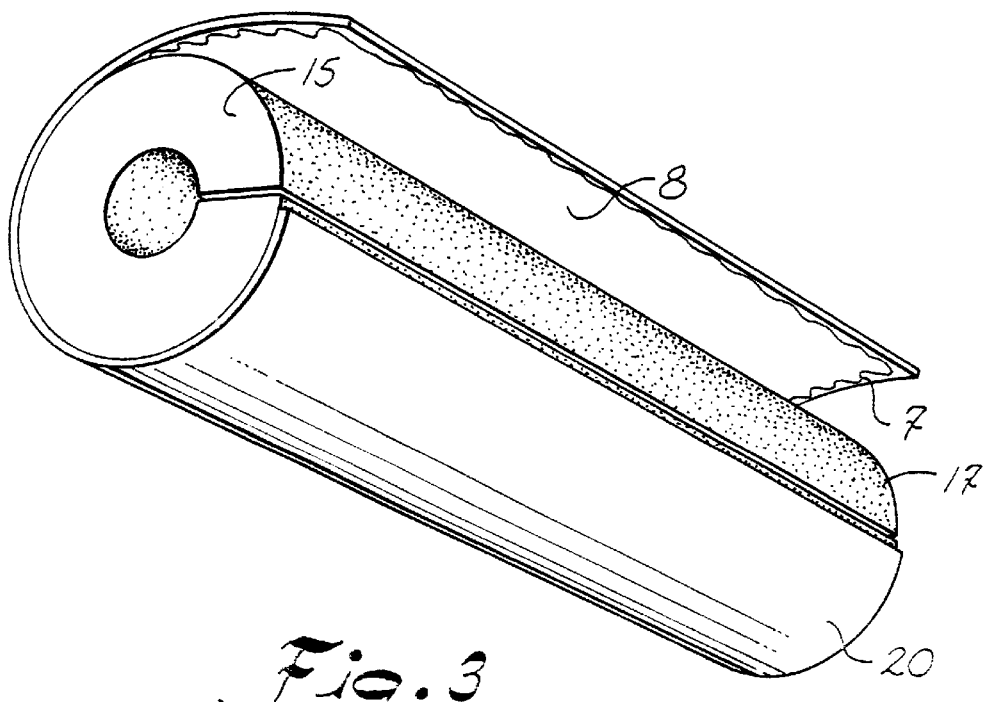
FIG. 3 is a perspective view of the preformed object being rolled with the Silicone Resistant Material being used to press the layer of silicone against the surface of the preformed object.

One method of applying the needed pressure to the material 15 against the silicone layer 7 is shown in FIG. 3, which includes rolling the material 15 such that the underside 20 of the Silicone Resistant Material 2, which does not have any silicone material 1 placed against it, is now exposed. The underside 20 can be used to roll the material 15, which is now held inside of the Silicone Resistant Material 2, to produce an even amount of pressure to assist the adhesion or bonding of the silicone layer 7 to the contacting surface 17 of the material 15.

After the material 15 has been pressed against the silicone layer 7 and the silicone layer 7 has bonded to the contacting surface 17, the Silicone Resistant Material 2 can be removed or peeled away from the silicone layer 7. The silicone layer 7 remains bonded against the contacting surface 17 and forms a uniform skin or coating layer to the material 15.

Figure 4A:
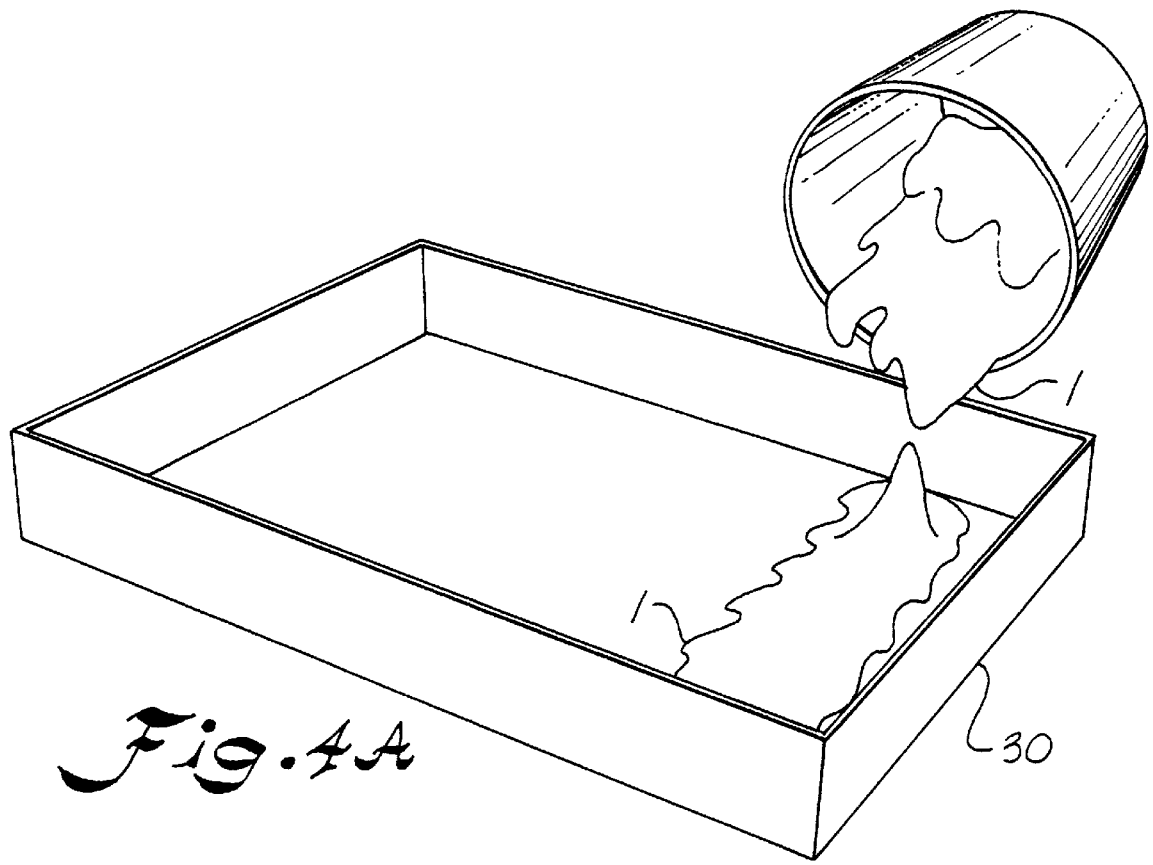
FIGS. 4A and 4B are perspective views of silicone foam or silicone rubber being placed inside of an open mold with the silicone foam or silicone rubber being spread within the mold to form a layer of silicone to cover the sides and bottom surfaces of the mold.
Figure 4B:
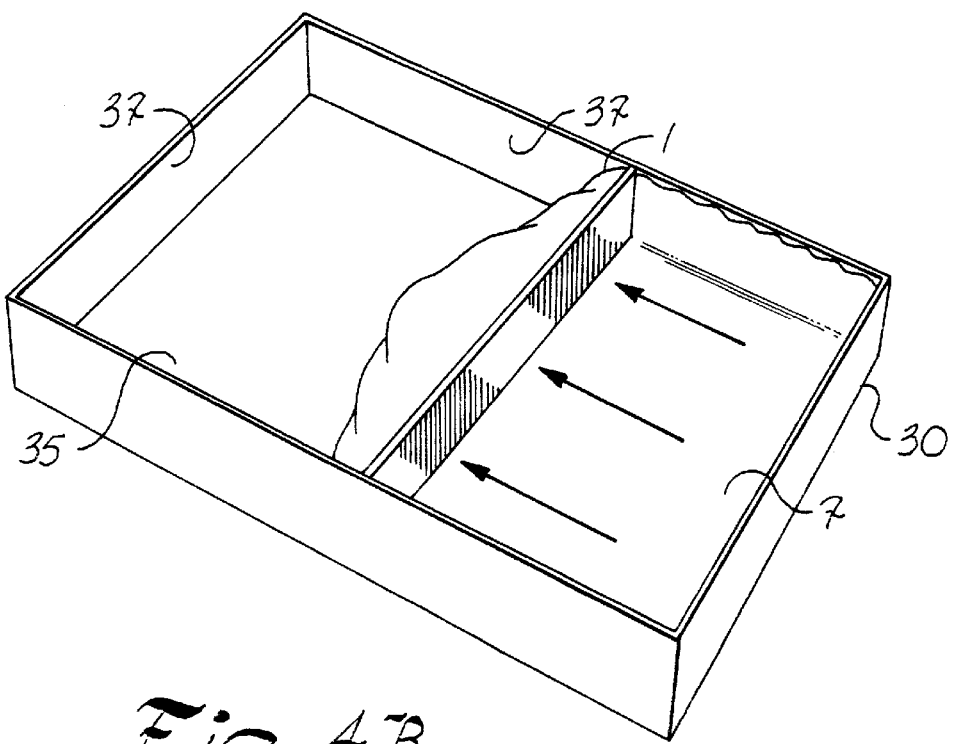

A further embodiment of the invention is shown in FIGS. 4A, 4B, 5 and 6. Referring to FIGS. 4A and 4B, the silicone material 1 is poured or placed within a mold or container 30 made from Silicone Resistant Material 2. A blade or spatula 31 that expends across the inside width and sides of the container 30 is placed in the container 30. As shown in FIG. 4B, the blade or spatula 31 is then used to evenly spread the silicone material 1 along the inside bottom surface 35 of the container 30, as well as evenly spread the silicone material 1 along the inside walls 37 of the container 30 to form the silicone layer 7. As previously discussed, the silicone layer 7 can have a thickness that ranges from approximately $\frac{1}{32}$ of an inch to one-half or more inches depending on the desired thickness and the amount of protective coating needed for the material 15. The silicone layer 7 is then allowed to cure for the approximate thirty seconds to seven minute time frame.

As shown in FIG. 6, the material 15 is placed inside the container 30. The container 30 can also have a top portion 50 (not shown) that can have a silicone layer 7 placed inside the top portion 50 which can then be placed over the material 15 to completely enclose the material 15. The material 15 should be pressed against the silicone layer 7 for the approximate twenty minutes to twenty-four hours time frame.

As shown in FIG. 5, to provide an additional cushioning protective feature to the material 15, cut or chopped particles 45 of silicone foam or silicone rubber, or other cushioning material, can be evenly placed on the top surface 8 of the silicone layer 7 prior to placing and pressing the material 15 against the silicone layer 7. The material 15 when placed inside the container 30 needs to be gently pressed against the silicone layer 7 for the approximate twenty minutes to twenty-four hours time frame. The container 30 is then removed from the now coated material 15, which now has a uniform skin or coating formed by the silicone layer 7. The uniform skin can have a texture that has features such as being smooth, shinny, scored, patterned, matted, or dull, and which provides protection to the integrity of the underlying shape. The uniform skin acts as a firewall and provides protection against corrosive chemicals and environmental degeneration to the material 15 from ultra violet light. Additionally, the silicone layer 7 can have a tear resistant feature and be formed with an imbedded fine wire mesh, optical fibers and/or pressure, temperature and/or light sensors that can be connected to a computer for providing data relating to pressure, temperature and/or light (not shown).

Figure 7:
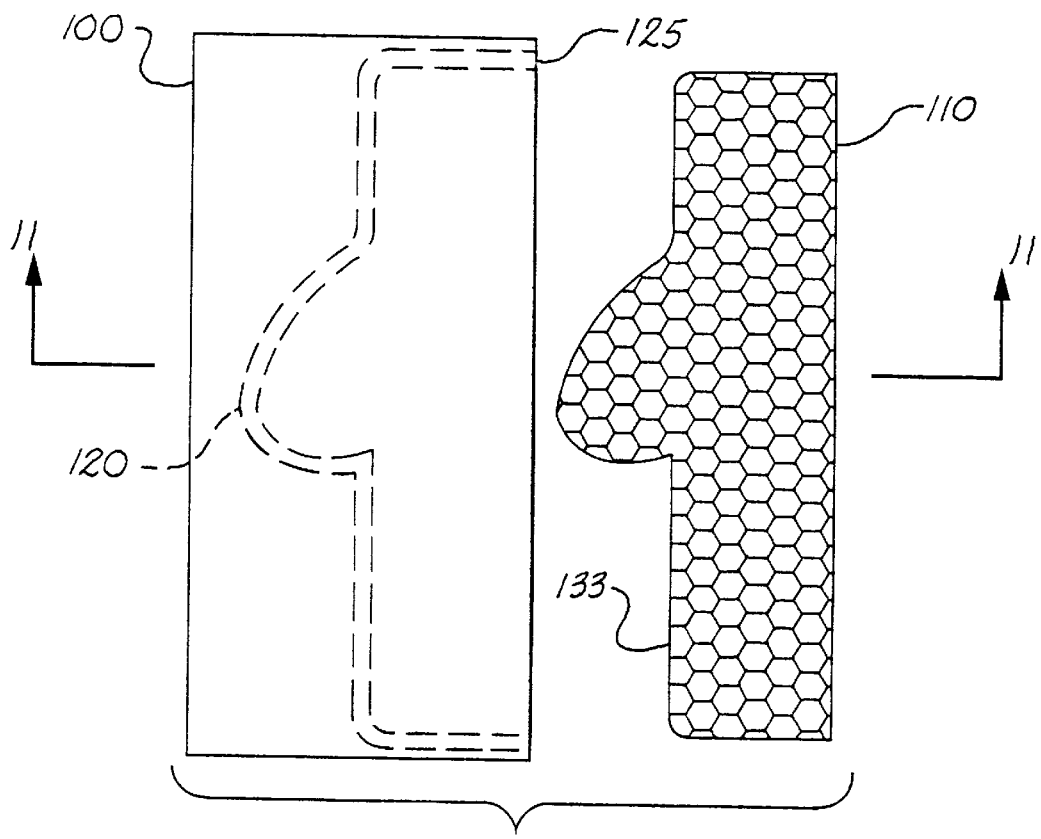
FIG. 7 is an elevational side view of an object to be coated and a detail and skinning mold, which has been applied with a silicone foam or silicone rubber material to form a skin of a predetermined thickness.
Figure 9:
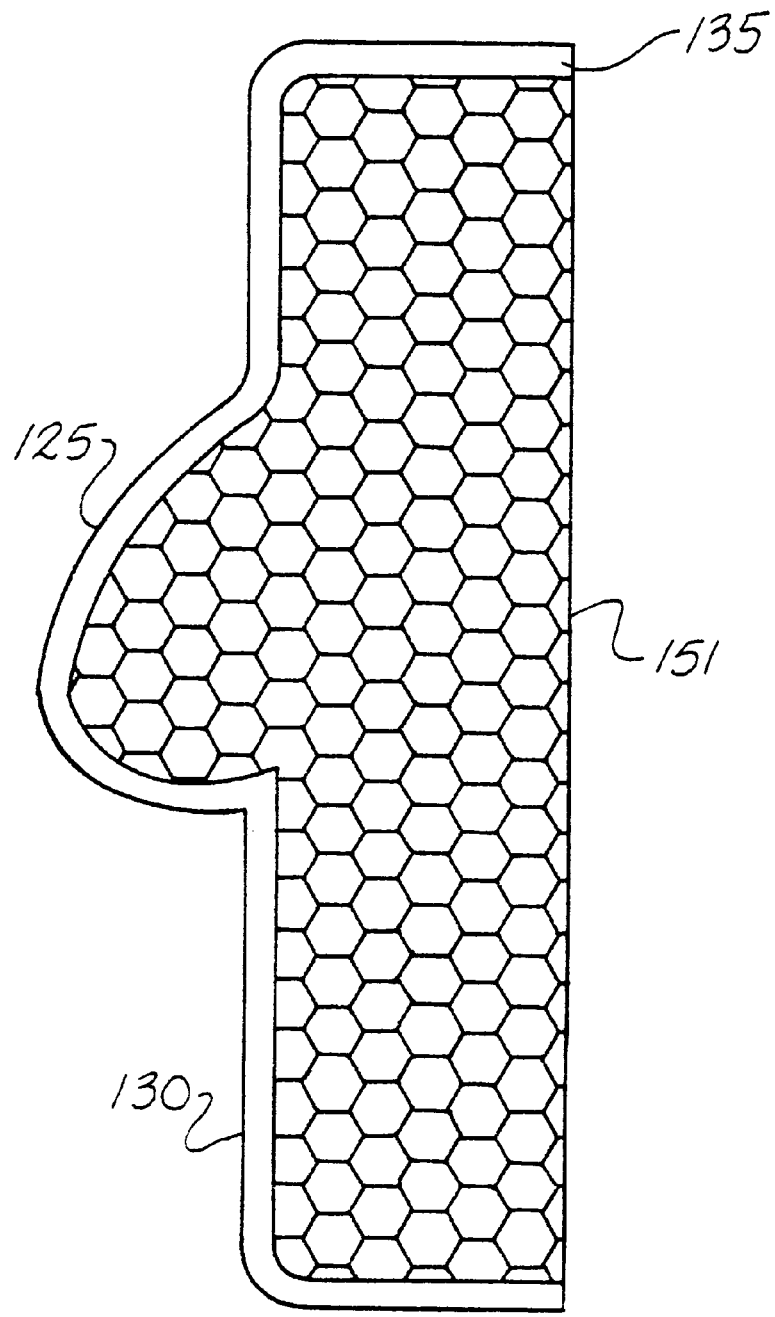
FIG. 9 is an elevational side view of an object with a silicone skin layer.
Figure 10:
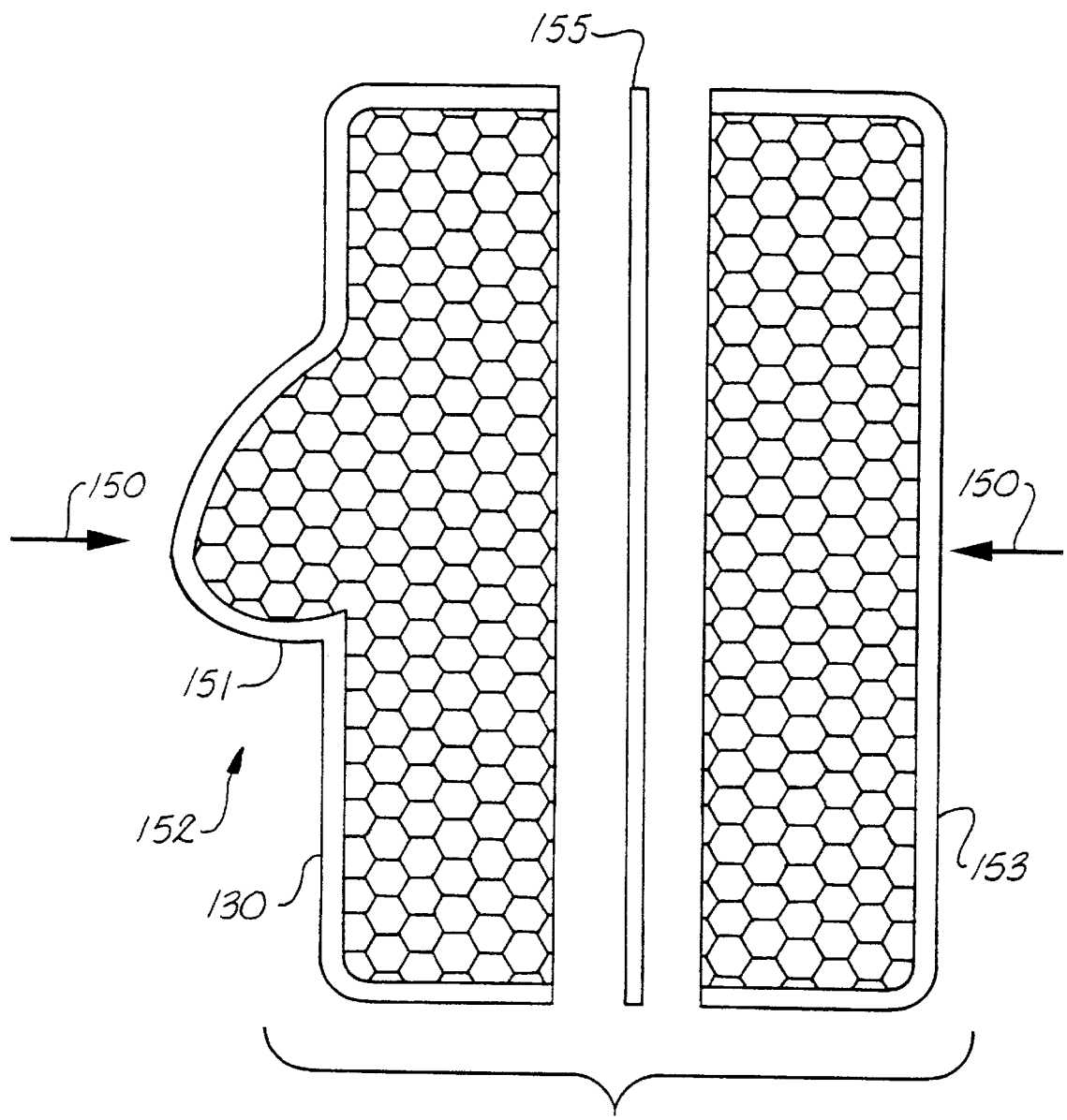
FIG. 10 is an elevational side view of two silicone skin layered pieces about to be bonded together.
Figure 11:
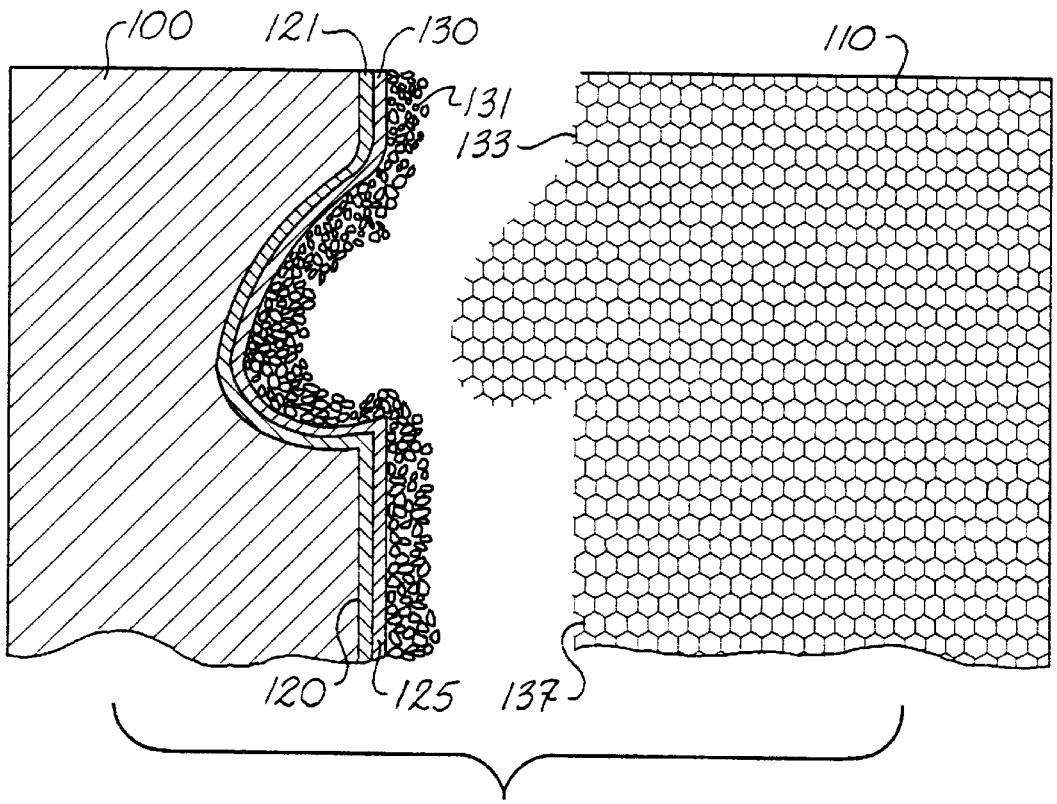
FIG. 11 is an elevational side view taken along lines 11—11 of FIG. 7, showing a detail view of a silicone skin layer forming against the inside surface of the detail and skinning mold and the object to be coated.

Referring to FIGS. 7–12, a third embodiment of the invention is shown. In FIG. 7, a detail and skinning mold 100 is shown. The detail and skinning mold 100 is an open air mold that has the same detailed characteristics as a model that has been sculpted with the desired precise shape and features. The detail and skinning mold 100 is made with a material that can be formed to have the desired shape of an article, such as a female torso. In the preferred embodiment, the detail and skinning mold 100 has an overlaid fiberglass soaked webbing that is resistant to silicone rubber or silicone foam. The detail and skinning mold 100 can be made of other materials. The detail and skinning mold 100 should be constructed, however, of sturdy material that is capable of withstanding the pressure from applying an object 110, which can be preshaped, into the detail and skinning mold 100. Also, the detail and skinning mold 100 should be able to comply with the use of release compounds. This is because, as shown in FIG. 11, the inner surface 120 of the detail and skinning mold 100 may be coated with a silicone releasing agent 121, such as Hexcel 8302 or Tetrafloroethylene Telomer Dispersion Dry Lubricant Release Agent, Camie A 1000, or a material resistant to adhesion to silicone foam or silicone rubber. A skinning silicone material 125, which is formulated similar to the silicone material 1, is then applied over the silicone releasing agent 121.

Figure 8:
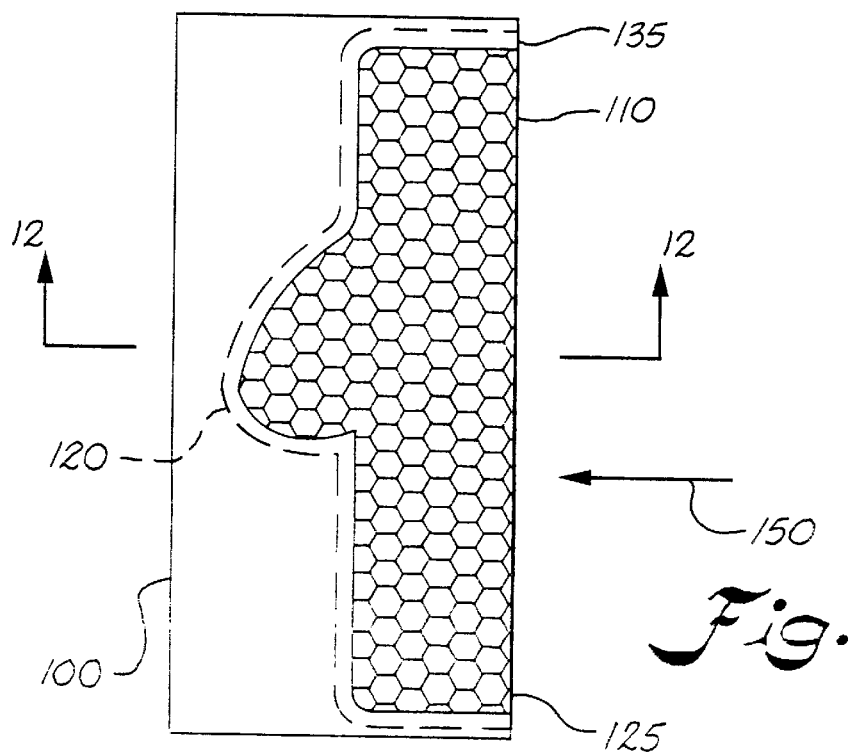
FIG. 8 is an elevational side view of an object being inserted and pressed into the detail and skinning mold, which has been applied with the silicone foam or silicone rubber material to form a skin layer.
Figure 12:
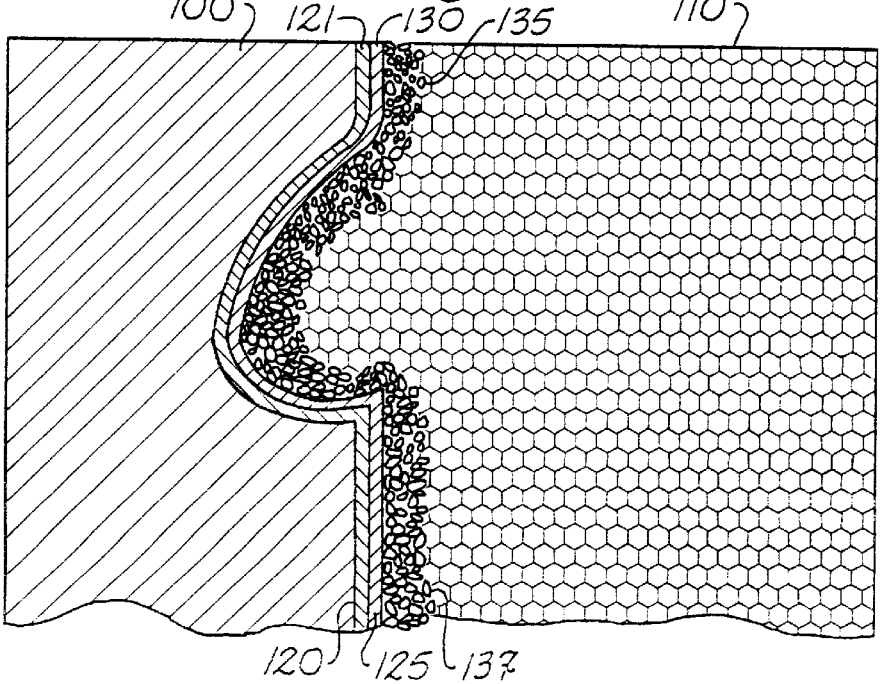
FIG. 12 is an elevational side view taken along lines 12—12 of FIG. 8, showing a detail view of the object being coated with the silicone layer and having the silicone skin layer bond to the object's outer surface to form a silicone skin layered piece.

As shown in FIGS. 8, 11 and 12, the object 110 is pressed into the detail and skinning mold 100 and against the skinning silicone material 125. The object 110 must be pressed into the detail and skinning mold 100 after the skinning silicone material 125 has started to cure, which is approximately thirty seconds to seven minutes after being applied to the releasing agent 121 (the "cure time"). As the skinning silicone material 125 is allowed to cure, an outer skin layer 130 is being formed against the silicone releasing agent 121. Also, during the cure process, an inner skin layer 131 is forming away from the inner surface 120 of the detail and skinning mold 100.

As shown in FIGS. 11 and 12, the object 110 must be pressed into the detail and skinning mold 100, before seven minutes have passed since the application of the skinning silicone material 125, to ensure a proper bonding between the skinning silicone material 125 and the outer surface 133 of the object 110. The cure time also allows the skinning silicone material 125 to blow into the outer surface 133 forming an interwoven bond 135. The outer surface 133 may have hollows 137 that are created by the cells formed in the outer surface 133 and which become filled with the inner skin layer 131 to form the interwoven bond 135. If the object 110 is pressed into the detail and skinning mold 100 after seven minutes have elapsed since the skinning silicone material 125 is applied, the interwoven bond 135 may not hold well under tension. Also, the interwoven bond 135 formed after seven minutes is not viscous enough to interweave and fill the hollows 137 of the outer surface 133.

If the object 110 is pressed into the detail and skinning mold 100, before the cure time has elapsed since the application of the skinning silicone material 125, the skinning silicone material 125 does not have enough time to cure and form the outer and inner skin layers 130 and 131, respectively. The object 110 when pressed into the detail and skinning mold 100 would then form a pocked and unattractive finish (not shown).

When the object 110 is pressed into the detail and skinning mold 100 within the cure time, the object 110 should be pressed with a constant and uniform pressure 150. The object 110 should be pressed into the detail and skinning mold 110 for approximately twenty minutes to twenty-four hours, depending on factors such as the thickness of outer and inner skinning layers 130 and 131, to allow the interwoven bond 135 to form (the "bond time"). Due to the silicone releasing agent 121 or the material resistant to adhesion to silicone foam or silicone rubber, the object 110 can be easily removed from the detail and skinning mold 100, and, as shown in FIG. 9, becomes a skinned molded piece 151. As shown in FIG. 10, if it is desired to have an article 152 that consists of several skinned molded pieces, such as 151 and 153, the skinned molded pieces 151 and 153 can be pressed together, with a silicone foam bonding layer 155 being formed in between the skinned molded pieces 151 and 153, to form the article 152.

The detail and skinning mold 100 can also be designed such that it can consist of two or more detail and skinning molds 100 that can be attached and pressed together to form a complex desired configuration, such as the article 156 (not shown). After the bond time has elapsed, the detail and skinning mold 100 can be removed, having an article 156 ready for use.

Upon removal of the skinned molded piece 151 from the detail and skinning mold 100, the outer skin layer 130 will have the finishing detailing that was etched into the inner surface 120 of the detail and skinning mold 100. In the case of the female torso, the outer skin layer 130 would have a human skin texture, which has a matted patina surface and not a shiny reflective surface (not shown).

The outer skin layer 130 can also show structural details like the sternum, and the clavicle. If a skinned molded piece of a human hand was needed, the knuckle and fingernails could be realistically shown with all of the fold lines, wrinkles and surface changes. The skinned molded piece 151 can now be used as is, if that is the needed application, or it may be bonded to another skinned molded piece 153 to form the article 152. The skinned molded pieces 151 and 153 can have skeleton sections set in between them to meet the needs of the application.

An additional embodiment of the invention includes the use of the detail and skinning mold 100, except that the skinning silicone material 125 is applied directly to the preshaped object 110 (not shown). An outer skin layer 130 is formed on the outer surface of the object 110. The layered preshaped object is then pressed into the detail and skinning mold 100. The outer skin layer 130 on the outer surface of the object 110 is allowed to set and bond to the outer surface of the object 110 for the bond time. The layered preshaped object is then removed from the detail and skinning mold 100 to form a skin molded piece 151, with the outer skin layer 130 having the finishing detailing that was etched into the inner surface 120 of the detail and skinning mold 100.

SUMMARY

The above-described method for coating objects with silicone foam or silicone rubber, such that the objects 15 have a silicone layer 7, includes the steps of: (i) applying silicone material 1 to the top surface 5 of Silicone Resistant Material 2; (ii) evenly spreading the silicone material 1 to form the silicone layer 7 on the top surface 5; (iii) allowing the silicone layer to sufficiently cure; (iv) gently pressing the object on to the top surface 8 of the silicone layer 7; (v) allowing the silicone layer 7 to adhere or bond to the object 15; and (vi) removing the silicone resistant material 2 from the non-bonded surface of the silicone layer 7. Additionally, the above-described method for coating objects with silicone foam or silicone rubber can be used in connection with a detail and skinning mold 100, and would include the steps of: (i) applying silicone material 125 to the inner surface 120 of the detail and skinning mold 100; (ii) allowing the silicone material 125 to sufficiently cure; (iii) pressing an object 110 into the skinning and detail mold 100; (iv) allowing the silicone material 100 to form an outer skin layer 130 that is bonded to the outer surface 133 of the object 110; and (v) removing the object 110 that now has an outer skin layer 130 from the skinning and detail mold 100.

Alternatively, the above-described method for coating objects with silicone foam or silicone rubber can include the steps of: (i) preshaping a core object of silicone adhesive material; (ii) applying a layer of silicone material to the preshaped object; (iii) pressing the layered preshaped object into a detail and skinning mold; (iv) allowing the layer of silicone material to bond to the outer surface of the preshaped object; and (v) removing the layered preshaped object from the mold, with the layer of silicone material having acquired the specific attributes of the inside surface of the mold.

It is to be understood that while certain forms of this invention have been illustrated and described, the invention is not limited thereto, except insofar as such limitations are included in the following claims.

What is claimed and described to be secured by Letters Patent is as follows:

1. A method for coating objects with silicone, the method having the steps of:
   a. applying a silicone material onto a top surface of a first silicone adhesive resistant material;
   b. forming a first silicone layer on the top surface of the first silicone adhesive resistant material, the first silicone layer having spaced apart top and bottom surfaces, the bottom surface being adjacent to the top surface of the first silicone adhesive resistant material and the top surface being bondable to an object;
   c. allowing the first silicone layer to sufficiently cure to allow for bonding to an object;
   d. placing the object having spaced apart first and second surfaces on to the bondable top surface of the first silicone layer, the first surface of the object being placed immediately adjacent to the bondable top surface;
   e. applying pressure to the second surface of the object;
   f. allowing the bondable top surface of the first silicone layer to bond to the object; and
   g. removing the first silicone adhesive resistant material from the bottom surface of the first silicone layer.

2. The method for coating objects with silicone as set forth in claim 1, wherein the first silicone layer is allowed to cure for approximately thirty seconds to seven minutes and the bondable top surface of the first silicone layer is allowed to bond to the object for approximately twenty minutes to twenty-four hours.

3. The method for coating objects with silicone as set forth in claim 1, wherein the silicone material is spread onto the top side surfaces of the first silicone adhesive resistant material.

4. The method for coating objects with silicone as set forth in claim 1, wherein the method includes the step of rolling the object with the attached first silicone layer to provide a uniform constant pressure to the bondable top surface of the first silicone layer.

5. The method for coating objects with silicone as set forth in claim 1, wherein the method includes the steps of (a) spreading the silicone material onto a bottom surface of a second silicone adhesive resistant material to form a second silicone layer having a bondable bottom surface; (b) allowing the second silicone layer to sufficiently cure to allow for bonding to an object; (c) pressing the bondable bottom surface of the second silicone layer to the second surface of the object; (d) allowing the bondable bottom surface of the second silicone layer to bond to the second surface of the object; and
   (e) removing the second silicone adhesive resistant material from the second silicone layer.

6. The method for coating objects with silicone as set forth in claim 1, wherein the first silicone adhesive resistant material has a pre-shaped pattern formed on the inside surfaces of the first silicone adhesive resistant material and the bottom surface of the first silicone layer acquires the pre-shaped pattern.

7. The method for coating objects with silicone as set forth in claim 1, wherein the bottom surface of the first silicone layer has the designed texture characteristics of the first silicone adhesive resistant material.

8. The method for coating objects with silicone as set forth in claim 1, wherein the bottom surface of the first silicone layer has the physical characteristics of the first silicone adhesive resistant material.

9. A method for coating objects with silicone, the method having the steps of:
   a. applying a silicone material onto a top surface of a first silicone adhesive resistant material;
   b. forming a first silicone layer onto the top surface of the first silicone adhesive resistant material, the first silicone layer having spaced apart top and bottom surfaces, the bottom surface being adjacent to the top surface of the first silicone adhesive resistant material and the top surface being bondable to an object;
   c. allowing the first silicone layer to sufficiently cure for approximately thirty seconds to seven minutes to allow for bonding to an object;
   d. placing the object having spaced apart first and second surfaces on to the bondable top surface of the first silicone layer, the first surface of the object being placed immediately adjacent to the bondable top surface;

e. applying pressure to the second surface of the object;

f. allowing the bondable top surface of the first silicone layer to bond to the object for approximately twenty minutes to twenty-four hours; and g. removing the first silicone adhesive resistant material from the bottom surface of the first silicone layer, wherein the bottom surface of the first silicone layer has the texture characteristics of the first silicone adhesive resistant material.

10. The method for coating objects with silicone as set forth in claim 9, wherein the method includes the step of rolling the object with the attached first silicone layer to provide a uniform constant pressure to the bondable top surface of the first silicone layer.

11. The method for coating objects with silicone as set forth in claim 9, wherein the silicone material is spread onto the top side surfaces of the first silicone adhesive resistant material.

12. The method for coating objects with silicone as set forth in claim 9, wherein the method includes the steps of (a) spreading the silicone material onto the bottom surface of a second silicone adhesive resistant material to form a second silicone layer having a bondable bottom surface; (b) allowing the second silicone layer to sufficiently cure to allow for bonding to the object; (c) pressing the bondable bottom surface of the second silicone layer to the second surface of the object; (d) allowing the bondable bottom surface of the second silicone layer to bond to the second surface of the object; and (e) removing the second silicone adhesive resistant material from the second silicone layer, wherein the top surface of the second silicone layer has the texture characteristics of the second silicone resistant material.

13. The method for coating objects with silicone as set forth in claim 9, wherein the first silicone adhesive resistant material has a pre-shaped pattern formed on the inside surfaces of the first silicone adhesive resistant material and the bottom surface of the first silicone layer acquires the pre-shaped pattern.

14. A method for coating objects with silicone, the method having the steps of:

a. applying a silicone material onto the top and side surfaces of a first silicone adhesive resistant material;

b. forming a first silicone layer on the top and side surfaces of the first silicone adhesive resistant material, the first silicone adhesive layer having a bottom surface adjacent to the top and side surfaces of the first silicone resistant material and a bondable top surface spaced apart from the bottom surface;

c. applying the silicone material on to the bottom surface of a second silicone adhesive resistant material to form a second silicone layer having a bondable bottom surface;

d. allowing the first and second silicone layers to sufficiently cure for approximately thirty seconds to seven minutes to allow for bonding to an object;

e. placing an object having spaced apart first and second surfaces on to the bondable top surface of the first silicone layer, the first surface of the object being placed immediately adjacent to the top surface;

f. placing the bondable bottom surface of the second silicone layer on to the second surface of the object;

g. applying a first pressure against the bottom surface of the first silicone adhesive resistant material and a second pressure against the top of the second silicone adhesive resistant material for pressing the respective first and second silicone layers against the object;

h. allowing approximately twenty minutes to twenty-four hours for the respective first and second silicone layers to bond to the object; and i. removing the first and second silicone adhesive resistant materials from the respective bottom surface of the first silicone layer and the top surface of the second silicone layer.

15. The method for coating objects with silicone as set forth in claim 14, wherein the first and silicone adhesive resistant materials have first and second pre-shaped patterns, respectively, formed on the inside surfaces of the first and second silicone adhesive resistant materials, respectively, and the bottom and top surfaces of the first and second silicone layers, respectively, acquire the respective first and second pre-shaped patterns.

16. The method for coating objects with silicone as set forth in claim 14, wherein the bottom and top surfaces of the first and second silicone layers, respectively, have the physical and texture characteristics of the respective first and second silicone adhesive resistant materials.

17. A method for coating objects with silicone, the method having the steps of:

a. applying a silicone material into a mold having a cavity having specific attributes of an article;

b. allowing the silicone material to sufficiently cure to allow for bonding to an object;

c. pressing a first object having first and second outer surfaces into the mold;

d. allowing the silicone material to bond to the first outer surface of the first object and to form a silicone layer on the first outer surface; and e. removing the first object from the mold, wherein the silicone layer has the specific attributes of the article.

18. The method of claim 17 wherein the cavity has a surface resistant to adhesion to silicone material.

19. The method of claim 17 and including the step of allowing the silicone material to cure in the cavity for approximately thirty seconds to seven minutes prior to pressing the first object into the mold.

20. The method of claim 17 and including the steps of applying the silicone material to the outer surface of a second object; and pressing the outer surfaces of the first and second objects that have the silicone material together to form a first complex shape.

21. A method for coating objects with silicone, the method having the steps of:

a. applying a silicone material into a mold having a cavity having specific attributes of a first side of an article, the cavity having a surface resistant to adhesion to silicone material;

b. allowing the silicone material to cure for approximately thirty seconds to seven minutes;

c. pressing a first object having first and second outer surfaces into the mold;

d. allowing the silicone material to bond to the first outer surface of the first object for approximately twenty minutes to twenty-four hours to form a silicone layer on the first outer surface; and e. removing the first object from the mold to form a first silicone layered object, wherein the silicone layer has the specific attributes of the first side of the article.

22. The method of claim 21 including the steps of making a second silicone layered object having first and second outer surfaces with the second outer surface having a silicone layer having the attributes of the second side of the article, applying the silicone mixture to the second outer surface of the first silicone layered object and to the first outer surface of the second silicone layered object, and pressing the second outer surface of the first silicone layered object and the first outer surface of the second silicone layered object together to form a first complex shape.

23. A method for coating objects with silicone, the method having the steps of:

a. preshaping a core object of silicone adhesive material;

b. applying a layer silicone material to the preshaped object;

c. pressing the layered preshaped object into a mold having the general physical characteristics of the preshaped object and the specific attributes of a detailed object;

d. allowing the layer of silicone material to bond to the surface of the pressed layered preshaped object; and e. removing the layered preshaped object from the mold, wherein the layer of silicone material has acquired the specific attributes of the detailed object.

* * * * *